US00PP26289P3

(12) United States Plant Patent
Pierron-Darbonne

(10) Patent No.: US PP26,289 P3
(45) Date of Patent: Jan. 5, 2016

(54) STRAWBERRY PLANT NAMED 'SAHARA'

(50) Latin Name: *Fragaria×ananassa*
Varietal Denomination: Sahara

(71) Applicant: Plantas de Navarra S.A., Navarra (ES)

(72) Inventor: Alexandre Pierron-Darbonne, Navarra (ES)

(73) Assignee: PLANTAS DE NAVARRA S.A. (ES)

( * ) Notice: Subject to any disclaimer, the term of this patent is extended or adjusted under 35 U.S.C. 154(b) by 50 days.

(21) Appl. No.: 13/987,147

(22) Filed: Jul. 3, 2013

(65) Prior Publication Data

US 2015/0020248 P1 Jan. 15, 2015

(51) Int. Cl.
*A01H 5/08* (2006.01)

(52) U.S. Cl.
USPC ..... Plt./208

(58) Field of Classification Search
USPC ..... Plt./208
CPC ..... A01H 5/0893
See application file for complete search history.

(56) References Cited

FOREIGN PATENT DOCUMENTS

| | | |
|---|---|---|
| ES | 20120164 | 6/2012 |
| MA | 461/13 | 5/2013 |
| QZ | 2012/1502 | 7/2012 |

OTHER PUBLICATIONS

UPOV Record Detail 2012.*
Fresh Fruit Portal, Mar. 19, 2013.*
"Planasa presenta dos nuevas variedades extra precoces", 6 Valencia Fruits, dated Mar. 5, 2013 (with English translation).

* cited by examiner

*Primary Examiner* — Keith O. Robinson
(74) *Attorney, Agent, or Firm* — Knobbe, Martens, Olson & Bear, LLP

(57) ABSTRACT

A new and distinct strawberry variety, *Fragaria×ananassa*, cv. 'Sahara' is characterized by an early time of flowering, an early time of ripening, an RHS red group (near 41 C to 43 C) fruit flesh color, a terminal leaflet length to width ratio that is longer than broad, and a terminal leaflet base shape that is acute.

14 Drawing Sheets

Latin name of the genus and species claimed: *Fragaria× ananassa.*

Variety denomination: 'Sahara'.

BACKGROUND AND SUMMARY OF THE INVENTION

The present invention relates to a new and distinct strawberry variety. The varietal denomination of the new variety is 'Sahara'. The new variety was designated by the breeder as 'Sahara 06.43H.79'. The new variety of strawberry was created in a breeding program by crossing two parents in 2006 in Cartaya (Huelva), Spain; in particular, by crossing as seed parent an undistributed strawberry parent designated '02-125' (unpatented) and as pollen parent an strawberry parent designated '03.98' (unpatented). Each parent is a selection from breeder's program and has not been commercialized.

The resulting seedling of the new variety was grown and asexually propagated by runners in Cartaya (Huelva), Spain, 7° W., 37° N., 45 feet elevation. Propagation by runners included propagation runners, separately for each varieties, first into a Screen-House, and after in the fields. Clones of the new variety were further asexually propagated and extensively tested. Each variety was reproduced by stolons in the nurseries. In order to establish and bring to health the initial head clones, mother plants that had developed several several stolons were subjected to a heat treatment, or Thermoterapy, at 36° C.-37° C. for 3 to 4 weeks. After that treatment, apical meristems were cut and developed (1 apical meristem corresponding to 1 rooting plant) in an in vitro culture for 5 to 6 weeks. This propagation and testing has demonstrated that the combination of traits disclosed herein which characterize the new variety are fixed and retained true to type through successive generations of asexual reproduction.

Among the characteristics which appear to distinguish the new variety from its closest variety of which I am aware, 'Sabrosa' (U.S. Plant Pat. No. 16,558) is a combination of traits which include: a terminal leaflet length to width ratio that is longer than broad for the new variety, as compared to a ratio that is as long as broad for 'Sabrosa,' a terminal leaflet base shape that is acute as compared to obtuse for 'Sabrosa,' a fruit flesh color that is (RHS red group near 41 C to 43 C) as compared to RHS red group near 43 B for 'Sabrosa,' a fruit hollow center that is weakly expressed as compared to absent or very weakly expressed for 'Sabrosa,' and an early time of flowering (50% of plants at first flower) and early time of ripening (50% of plants with ripe fruit) as compared to medium times of flowering and ripening for 'Sabrosa.' The new variety is distinguished from its parents by the following characteristics possessed by 'Sahara' which are different than, or not possessed, by the seed parent designated '02-125' (unpatented) and the pollen parent designated '03-98' (unpatented). (1) Seed parent '02-125' (unpatented) is less vigorous than the plant of the new variety 'Sahara'. (2) Habit plant of seed parent '02-125' (unpatented) flat, whereas in the new variety 'Sahara' is globose. (3) In seed parent '02-125' (unpatented) the position of the inflorescence relative to the foliage is above, whereas in the new variety 'Sahara' is level with. (4)

In seed parent '02-125' (unpatented) the fruit size is smaller than in the new variety 'Sahara'. (5) In pollen parent '03-98' (unpatented) the plant is more dense and more vigorous that the new variety 'Sahara'. (6) In pollen parent '03-98' (unpatented) the fruit size is bigger than one of the new variety 'Sahara'. Moreover, the new variety 'Sahara' presents an early time of flowering and ripening, whereas in the pollen parent '03-98' (unpatented) time of flowering and ripening are medium.

The average fruit mass (g/fruit) observed for the new variety 'Sahara' on March 18 was 37.9 g, as compared to 39.3 g for 'Sabrosa' and 24.7 g for 'Camarosa' (U.S. Plant Pat. No. 8,708). The luminosity for the fruit of the new variety at 460 nm was 18.6, as compared to 27.3 for 'Sabrosa' and 31.5 for 'Camarosa.'

The accompanying photographs show typical specimens of the new variety, designated 'Sahara' or '06.43H.79' in the photographs.

BRIEF DESCRIPTION OF PHOTOGRAPHS

The accompanying photographs show typical specimens of the new variety, designated 'Sahara' or '06.43H.79' in the illustrations, including fruit, foliage and flower, in color as nearly true as it is reasonably possible to make in color illustrations of this character.

DESCRIPTION OF THE NEW VARIETY

Figure 1:
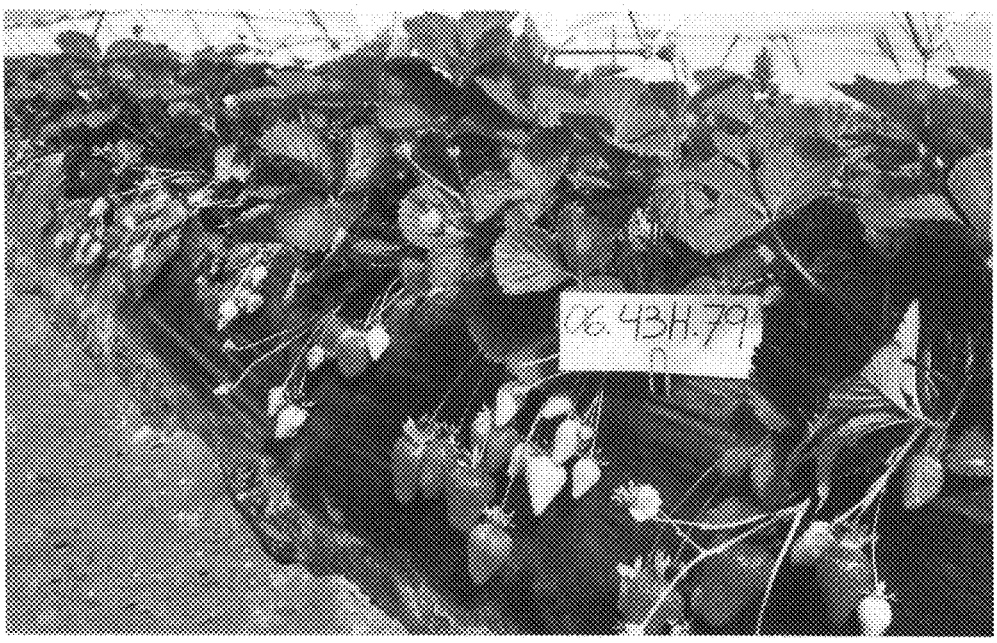
FIG. 1 shows several plants of the new variety 'Sahara.'
Figure 2:
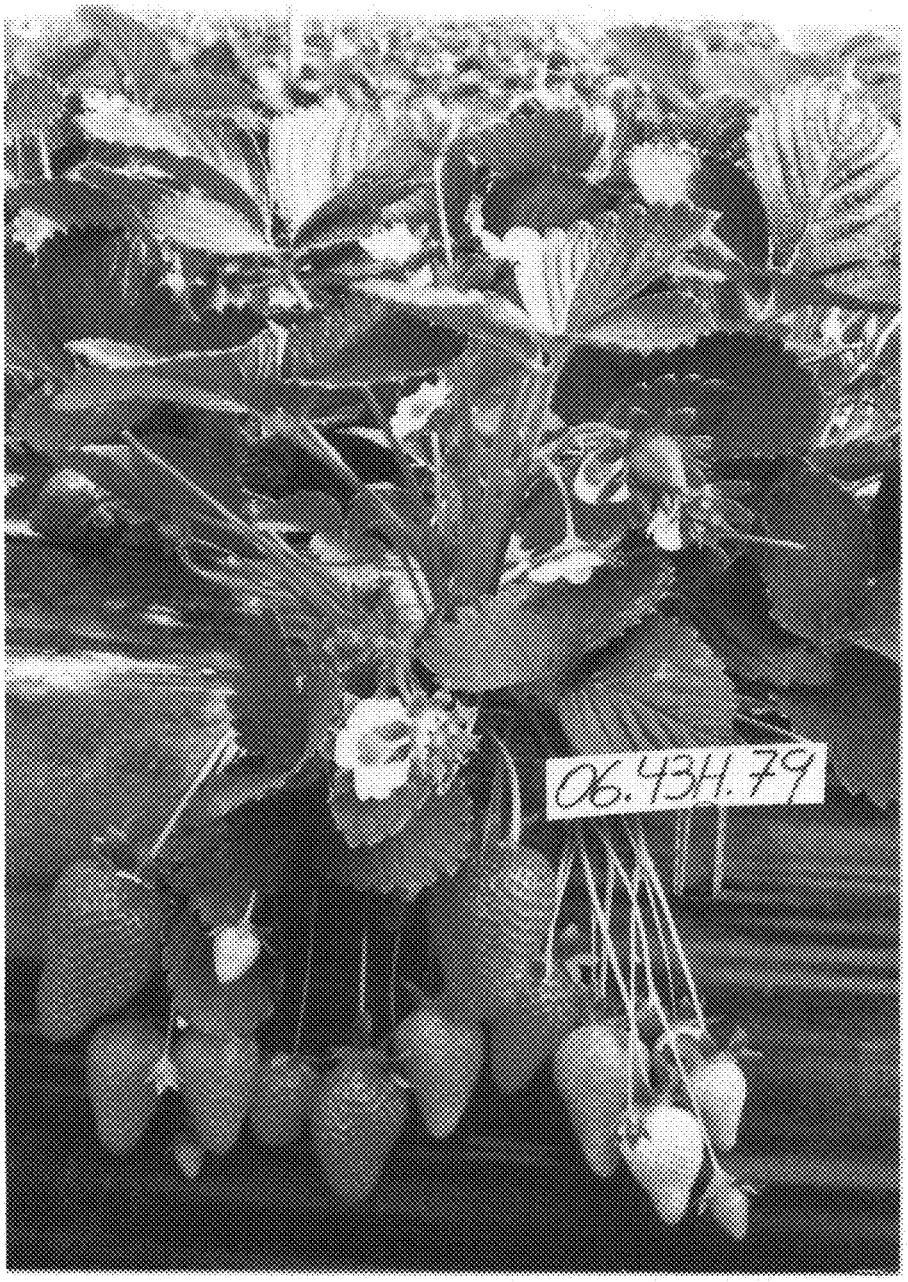
FIG. 2 shows several plants of the new variety 'Sahara.'
Figure 3:
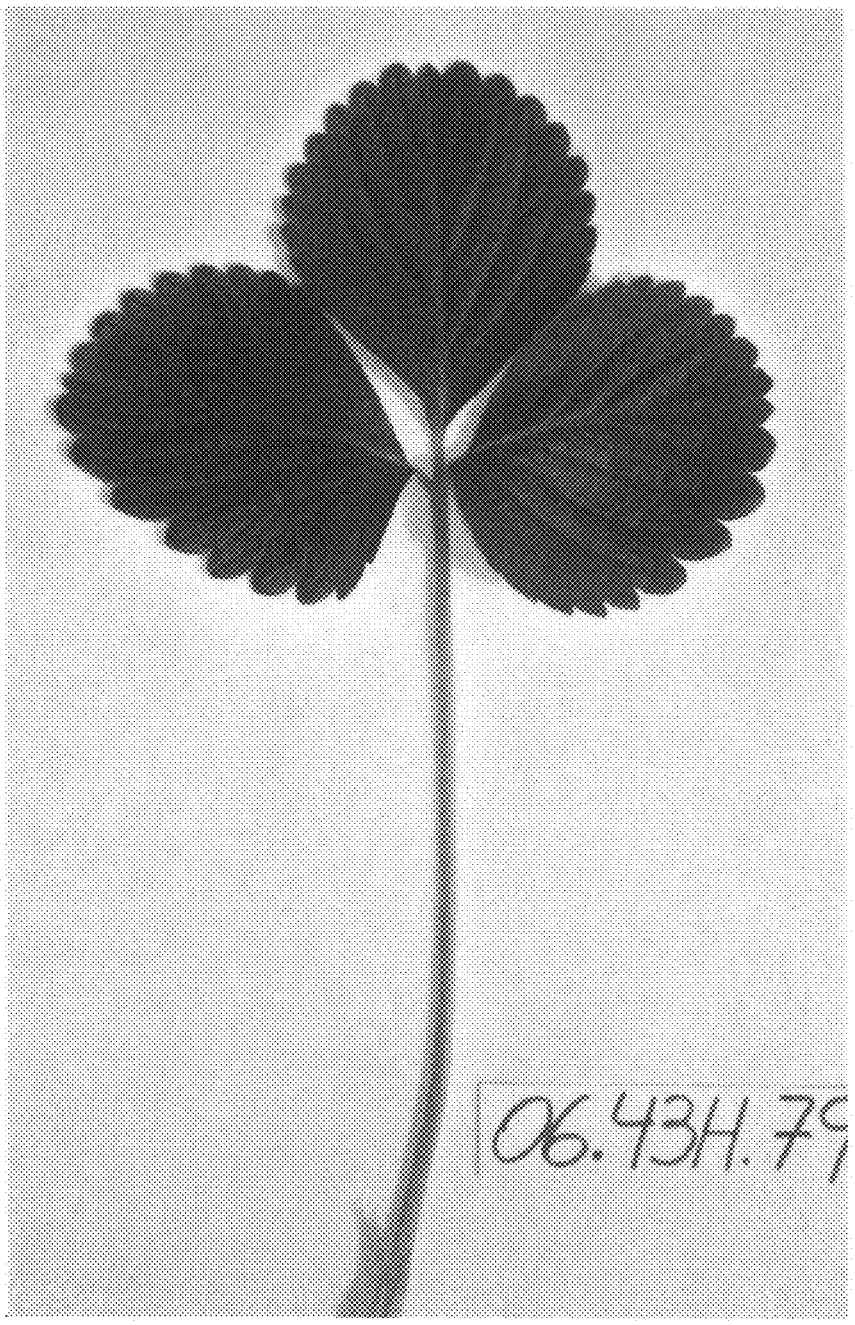
FIG. 3 shows the upper side of a complete leaf of the new variety 'Sahara.' A terminal leaflet length to width ratio that is longer than broad can be seen, as can a terminal leaflet base shape that is acute. A medium green color (RHS near 146 A to 147 A) can be seen.
Figure 4:
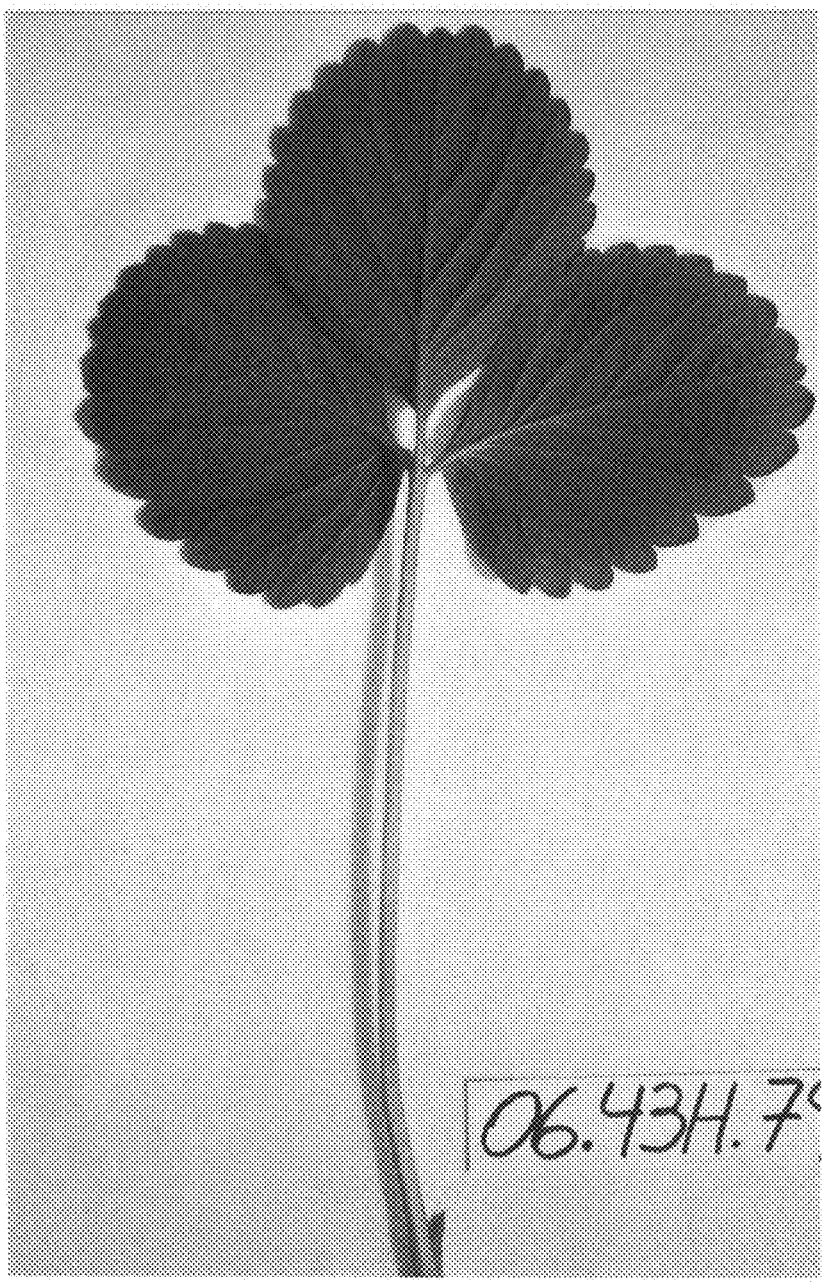
FIG. 4 shows the lower side of a complete leaf of the new variety, 'Sahara.' A slightly concave to flat cross-section can be seen.
Figure 5:
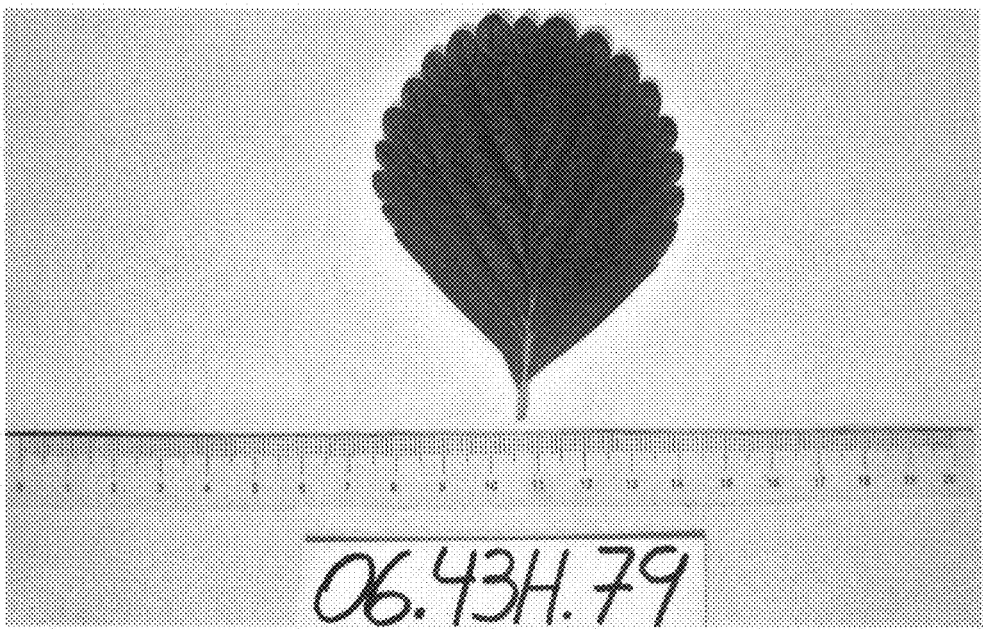
FIG. 5 shows the upper side of a terminal leaflet of the new variety 'Sahara.' A medium green color (RHS near 146 A to 147 A), and a crenate shape of incisions at the margin can be seen.
Figure 6:
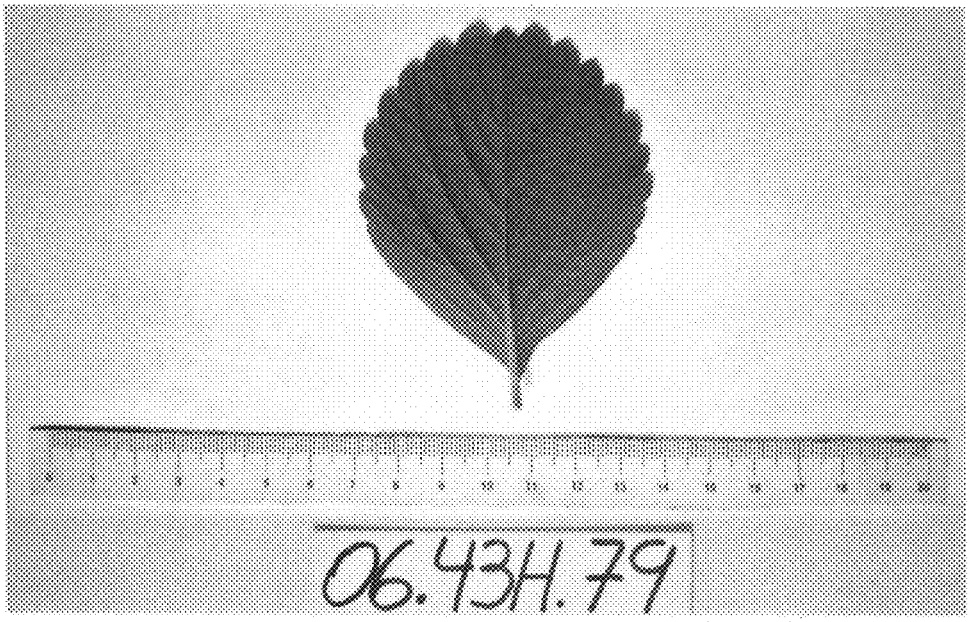
FIG. 6 shows the lower side of a terminal leaflet of the new variety 'Sahara.'
Figure 7:
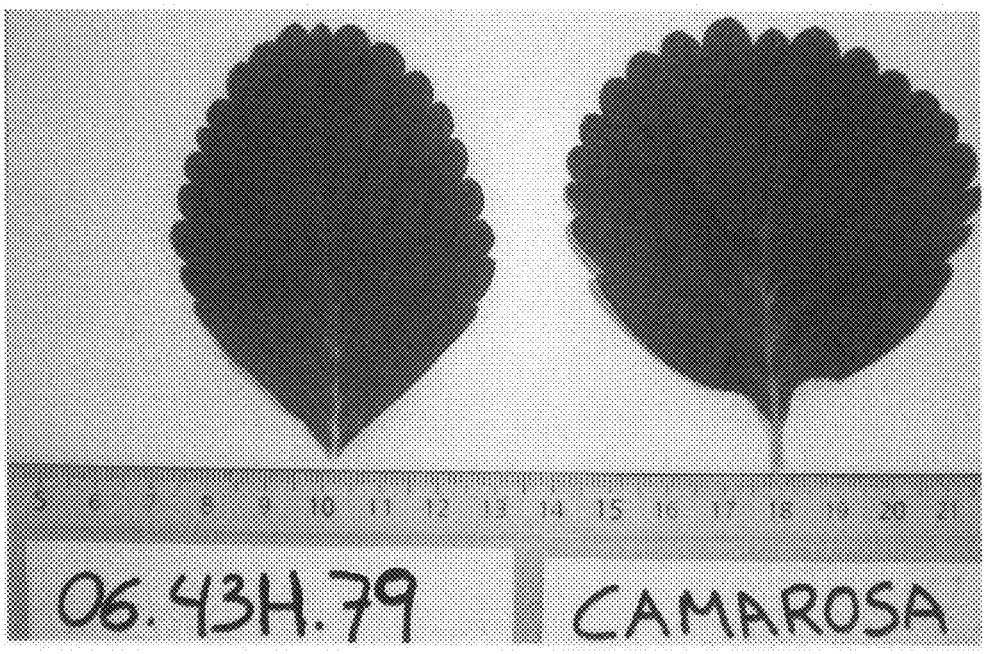
FIG. 7 shows the upper side of a terminal leaflet of the new variety 'Sahara' in comparison to that of 'Camarosa.'
Figure 8:
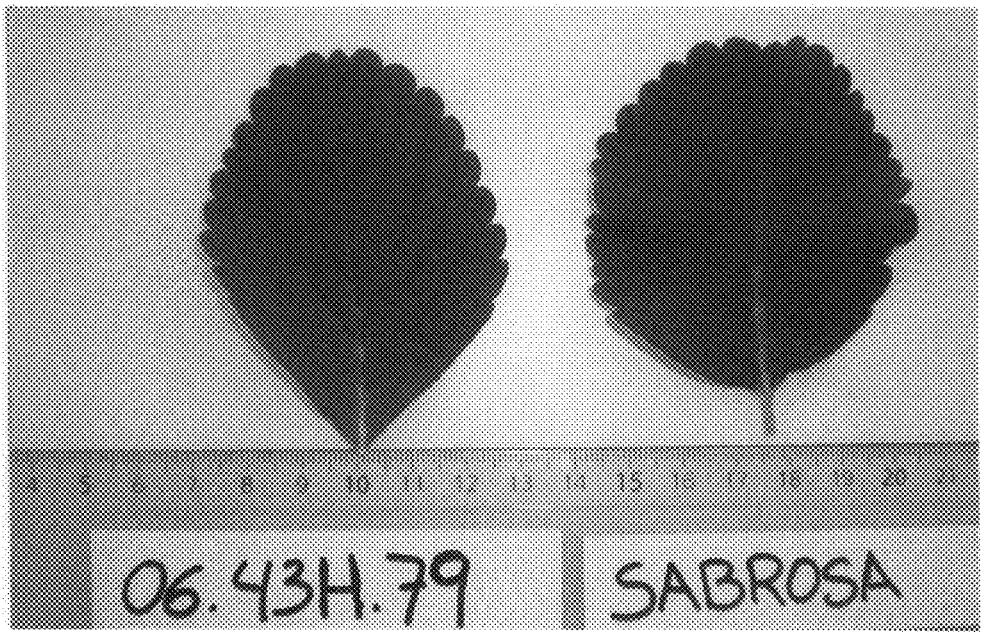
FIG. 8 shows the upper side of a terminal leaflet of the new variety 'Sahara' in comparison to that of 'Sabrosa.'
Figure 9:
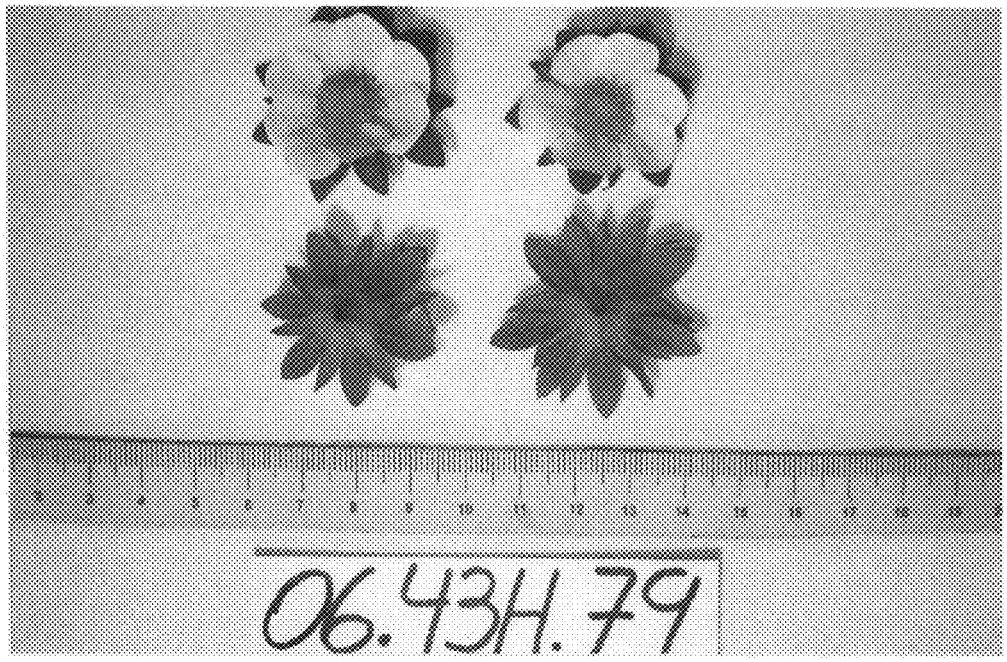
FIG. 9 shows the flower and calyx of the new variety, 'Sahara.'
Figure 10:
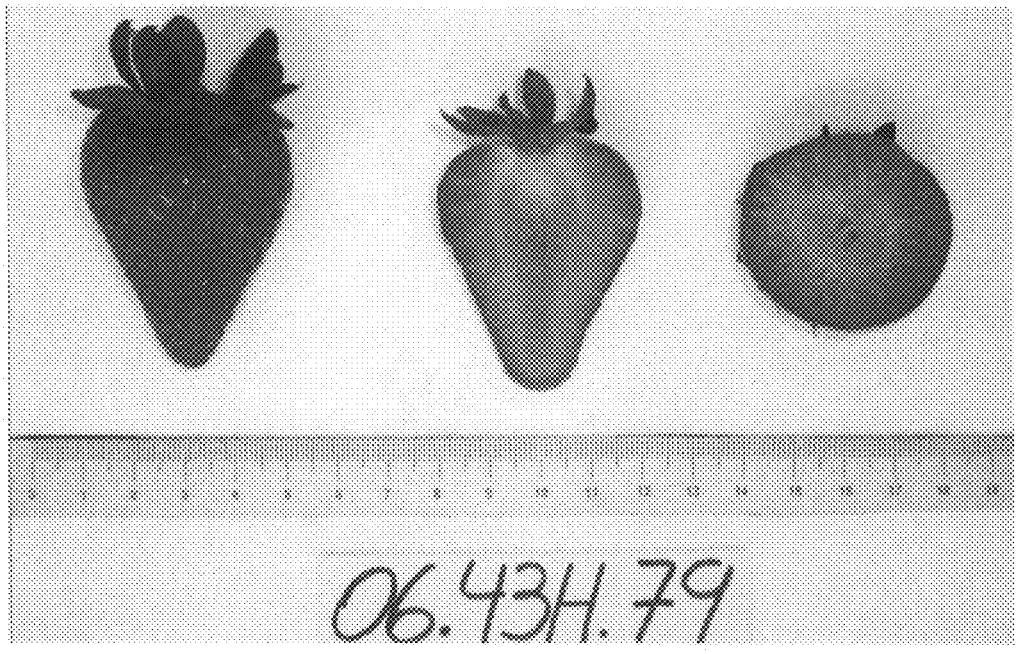
FIG. 10 shows a typical whole fruit and a sliced section of the fruit of the new variety 'Sahara.' In the whole fruit, a conical shape, red color (RHS near 42 A to 44 A), and medium glossiness can be seen. In the sliced section, the typical flesh coloration of about red (RHS red group (near 41 C to 43 C)) and a weakly expressed hollow center can be seen.
Figure 11:
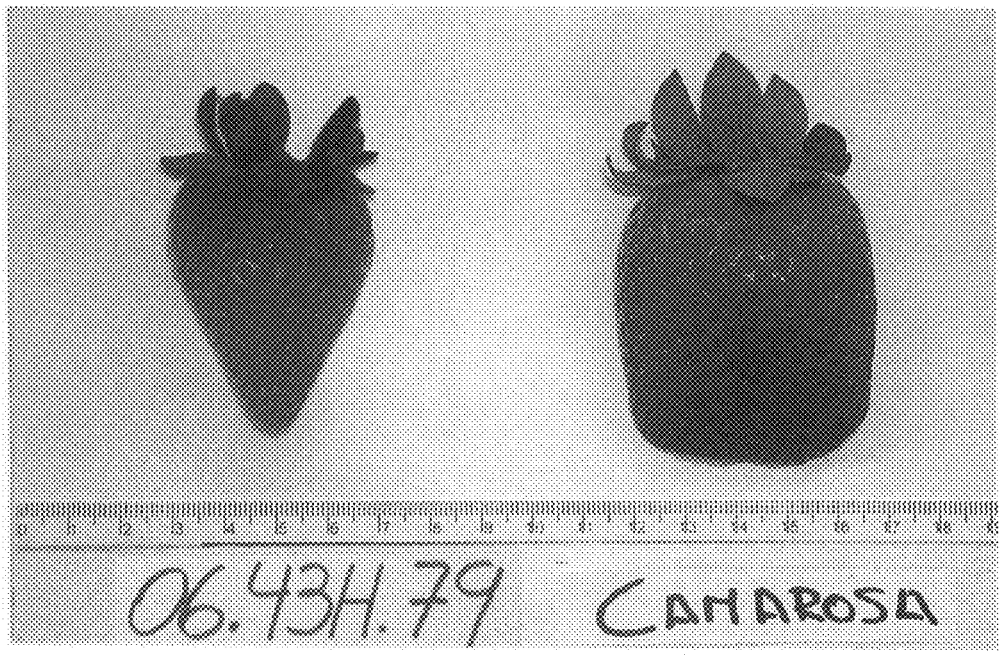
FIG. 11 shows typical whole fruit of the new variety 'Sahara' in comparison to that of the variety 'Camarosa.'
Figure 12:
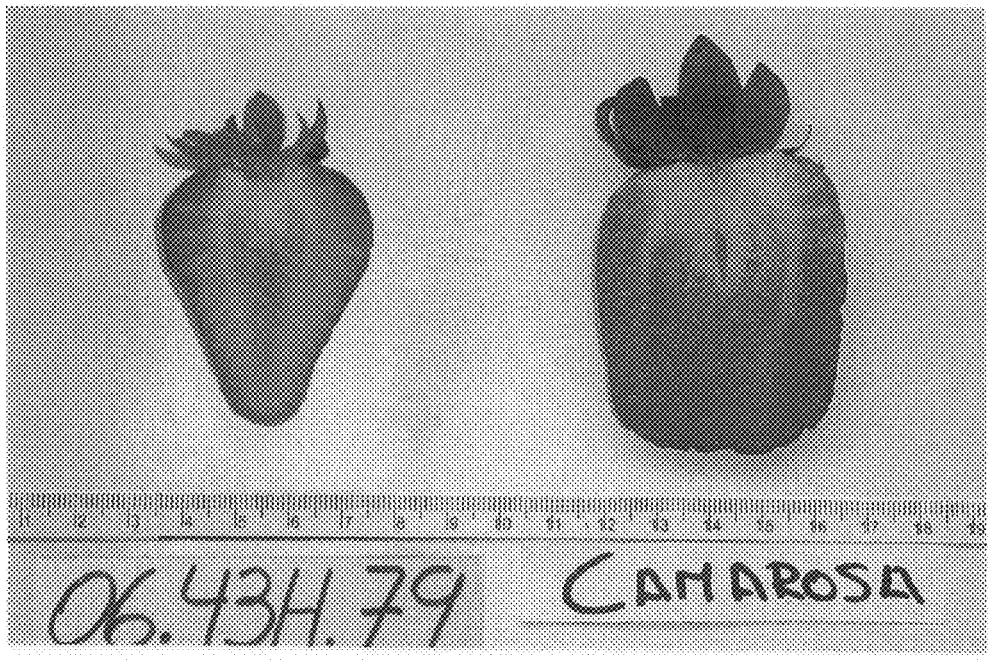
FIG. 12 shows typical sliced section of the new variety 'Sahara' in comparison to that of the variety 'Camarosa.'
Figure 13:
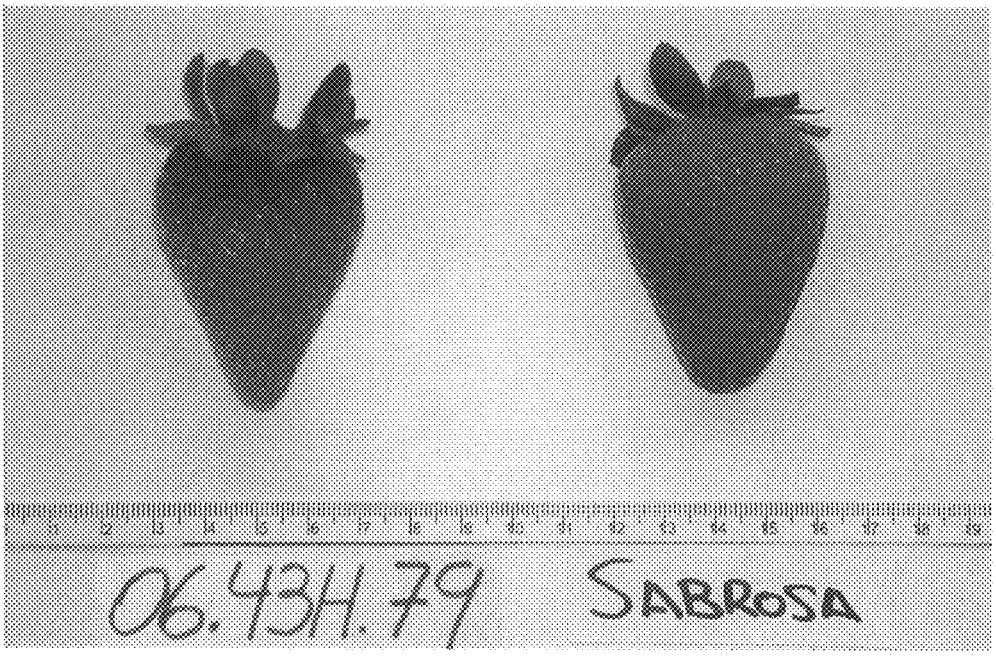
FIG. 13 shows typical whole fruit of the new variety 'Sahara' in comparison to that of the variety 'Sabrosa.'
Figure 14:
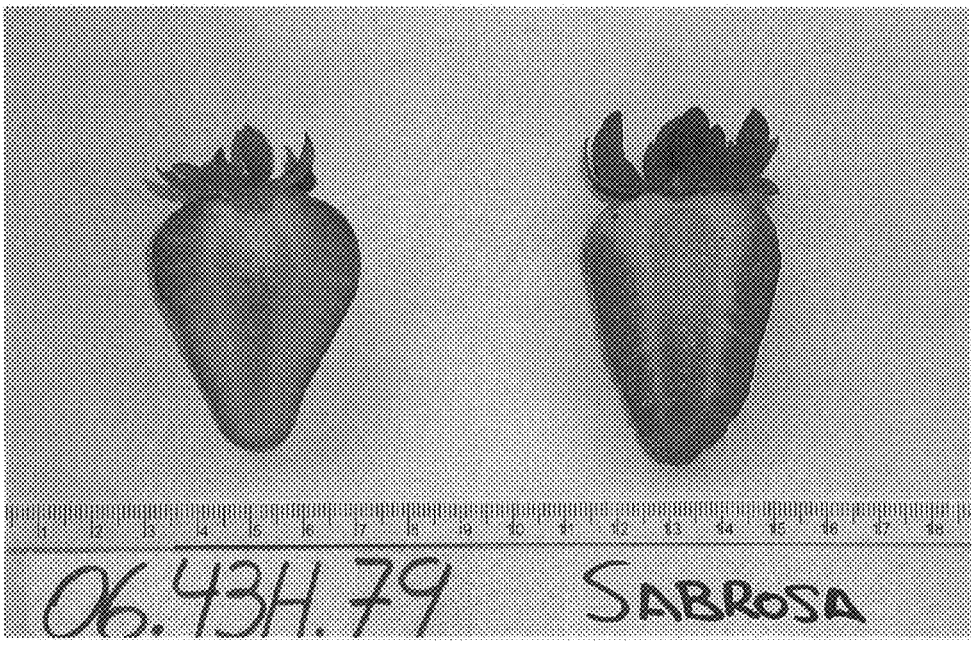
FIG. 14 shows typical sliced section of the new variety 'Sahara' in comparison to that of the variety 'Sabrosa.'

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1995. The color descriptions and other phenotypical descriptions may deviate from the stated values and descriptions depending upon variation in environmental, seasonal, climatic and cultural conditions.

The following detailed description of the new variety is based upon observations taken of plants and fruits grown in Cartaya (Huelva), Spain, 7° W., 37° N., 45 feet elevation.

The new variety is principally propagated by way of runners. Although propagation by runners is presently preferred, other known methods of propagating strawberry plants may be used. Strawberries root well after transplanting.

The term "blistering" used herein refers to the texture or rugosity or surface ondulation inherent to leaves and is generally a constant characteristic.

Table 1 shows the Weight (g/Fruit) at March 18 of the new variety 'Sahara' when compared its closest variety "Sabrosa," and another variety, "Camarosa."

TABLE 1

| WEIGHT (g/fruit)[i] | March 18 |
|---|---|
| Sahara | 37.9 |
| Sabrosa | 39.3 |
| Camarosa | 24.7 |

[i]WEIGHT is shown as the average weight per fruit in First Quality Fruits.

Table 2 shows a comparison of the fruit analysis on March 18 between the new variety 'Sahara,' its closest variety, "Sabrosa," and another variety, "Camarosa."

TABLE 2

| | SAHARA | SABROSA | CAMAROSA |
|---|---|---|---|
| Humidity & Volatile Matter (%) | 91.0 | 91.2 | 90.4 |
| Dry Matter (%) | 9.0 | 8.8 | 9.6 |
| pH (to 20°) | 3.8 | 3.7 | 3.7 |
| Acidity as Anhydride Citric (%) | 0.6 | 0.6 | 0.6 |
| Soluble solids (°Brix) | 7.9 | 7.0 | 7.5 |
| Maturity Index | 13.1 | 11.7 | 12.5 |
| Dominant Tonality (nm) | 490 | 495 | 495 |
| Luminosity: Transmittance to 460 nm | 18.6 | 27.3 | 31.5 |

Dry Matter: It is the weight of the residual left from the trituration of the fruit after the drying process at a temperature of 103° C. + 2° C. until reaching constant weight.

$$\% \text{ Dry Matter} = \frac{\text{Weight Dry Matter}}{\text{Weight Fresh Matter}} \times 100$$

Humidity & Volatile Matter: Represents the content in volatile matters and water of the fruits.

$$(\%) \text{ Humidity \& Volatile Matter} = 100 - \% \text{ Dry Matter}$$

Maturity Index: Relation between Soluble solids and Acidity as Anhydride Citric.

$$\text{Maturity Index} = \frac{\text{Soluble solids}}{\text{Acidity as Anhydride Citric}}$$

DETAILED DESCRIPTION OF THE NEW VARIETY

Plant:
- *Growth habit*.—Upright.
- *Habit*.—Globose.
- *Density*.—Open.
- *Vigor*.—Medium.
- *Height*.—About 20 cm.
- *Width*.—About 21 cm.
- *Number of crowns per plant*.—About 6 to 8 crowns per plant.

Stem:
- *Length*.—About 12 cm.
- *Pubescence*.—Sligthly outwards.
- *Color*.—RHS yellow-green group (near 145 A to 146 D).

Leaf:
- *Size*.—Large.
- *Upperside*.—RHS yellow-green group color (near 146 A to 147 A).
- *Underside*.—RHS yellow-green group color (near 146 A to 146 B).
- *Cross section*.—Slightly concave to flat.
- *Leaf surface ondulation or blistering*.—Weak.
- *Glossiness*.—Medium.
- *Leaf variegation*.—Absent.
- *Length*.—About 9 cm.
- *Width*.—About 13 cm.
- *Average number of serrations per leaf*.—About 16 to 18 serrations for each foliole (3 folioles per leaf).

Terminal leaflet:
- *Length/width ratio*.—Longer than broad.
- *Shape in cross section*.—Slightly concave to flat.
- *Shape of base*.—Acute.
- *Margin*.—Crenate.

Petiole:
- *Attitude of hairs*.—Slightly outwards.
- *Length*.—Long (about 12 cm).
- *Petiole diameter*.—About 2.0 to 3.0 mm.
- *Petiole texture*.—Slightly down and rigid.
- *Petiole color*.—RHS yellow-green group (near 145 A to 146 D).
- *Petiole pubescence*.—Slightly outwards.

Stipule:
- *Anthocyanin coloration*.—Weak.
- *Color*.—RHS greyed-red group coloration (near 179 D to 179 C).
- *Size*.—Medium.
- *Length*.—About 11.0 to 12.0 mm.
- *Width*.—About 2.8 to 3.5 mm.

Stolons:
- *Number*.—Medium, about 8.
- *Antocyanin coloration*.—Weak.
- *Color*.—RHS yellow-green group (near 146 D to 146 C).
- *Pubescence*.—Weak.
- *Average diameter at the bract*.—Medium, about 3.0 to 3.5 mm.

Inflorescence:
- *Position relative to foliage*.—Level with.
- *Number of flowers*.—Medium.

Flower:
- *Size*.—Medium.
- *Size of calyx relative to corolla*.—Same size.
- *Stamen*.—Present.
- *Average number of flowers per plant*.—About 56 to 60 flowers per plant.
- *Time from bloom to mature fruit* (*in Huelva, Spain*).—About 32 to 38 days.
- *Diameter primary flowers*.—About 2.9-3.2 cm.
- *Diameter secondary flowers*.—About 2.5-2.8 cm.
- *Arrangement of petals*.—Overlapping.
- *Diameter corolla primary flowers*.—About 2.9 to 3.2 cm.
- *Diameter corolla secondary flowers*.—About 2.5 to 2.8 cm.
- *Diameter calyx primary flowers*.—About 2.9 to 3.2 cm.
- *Diameter calyx secondary flowers*.—About 2.5 to 2.8 cm.
- *Color of receptacle*.—RHS red group (near 42 A to 44 A).
- *Color of anthers*.—RHS yellow group (near 12 C to 13 C) and darkening with advanced maturity.
- *Pollen*.—Fertile and abundant.
- *Pollen color*.—RHS yellow orange group (near 16 C to 16 B).
- *Number of pistils*.—Numerous.
- *Pistil size*.—Generally average in size.
- *Pistil color*.—RHS yellow group (near 13 C to 14 C).

Primary flower:
- *Relative positioning of petals*.—Overlapping.

Petal:
- *Length/width ratio*.—Broader than long.
- *Color*.—RHS white group (near 155 B to 155 A).
- *Length*.—Approximately 9 to 11 mm.
- *Width*.—Approximately 12 to 14 mm.
- *Shape*.—Slightly ovate.
- *Texture* (*both sides*).—Smooth, soft and slightly waved.
- *Number of petals per flower*.—About 6-8.

Fruit:
- *Ratio of length/width*.—Slightly longer than broad.
- *Color*.—RHS red group near 43 B to 41 A.
- *Size*.—Medium.
- *Difference in shapes between primary and secondary fruits*.—Moderate.
- *Band without achenes*.—Absent or very narrow.
- *Unevenness of surface*.—Weak.
- *Evenness of colour*.—Even.
- *Glosiness*.—Medium.
- *Insertion of achenes*.—Below surface.
- *Insertion of calyx*.—Level with fruit.
- *Attitude of the calyx segments*.—Reflexed.
- *Size of the calyx in relation to fruit diameter*.—Slightly smaller.
- *Adherence of calyx*.—Strong.
- *Firmness*.—Firm.
- *Colour of flesh*.—RHS red group (near 41 C to 43 C), lightening toward center.
- *Hollow center*.—Weakly expressed.
- *Color of core*.—RHS red group (near 41 D to 43 D).
- *Distribution of red colour of flesh*.—Only marginal.
- *Time of flowering*.—Early.
- *Tim of ripening*.—Early.
- *Type of bearing*.—Not remontant.
- *Shape*.—Conical.
- *Peduncle length of inflorescence stem*.—Primary fruit about 15 to 17 cm, secondary fruit about 10 to 12 cm.
- *Peduncle color*.—RHS yellow-green group (near 145 A to 146 D).
- *Primary fruit length*.—About 4.5-5.0 cm.

*Primary fruit width.*—About 3.5-4.0 cm.

*Secondary fruit length.*—About 4.0-4.5 cm.

*Secondary fruit width.*—About 3.0-3.5 cm.

*Color upper side of sepals.*—Green group (near 131 B to 135 A).

*Color underside of sepals.*—Green group (near 146 D to 147 C).

*Length of sepals.*—About 10 to 14 mm.

*Width of sepals.*—About 5 to 7 mm.

*Number of sepals per flower.*—The calyx presents 7 to 8 sepals with lanceolate shape and 6 to 8 sepals in addition smaller than above mencionated with pointed shape.

*Color of achenes.*—RHS orange red group (near 33 B to 33 A).

*Band without achenes.*—Absent or very narrow.

*Sweetness.*—Medium. 7.9° Brix.

*Acidity.*—Medium. 0.60% (Acidity as Anhydride Citric).

*Time of flowering* (50% *of plants at first flower*).—Early.

*Time of ripening* (50% *of plants with ripe fruits*).—Early.

*Type of bearing.*—Not remontant.

*Chilling.*—Weak.

Disease resistance: No particular sensitivity to any disease or parasite has been observed for 'Sahara'.

Cold tolerance: As the capacity of plant to develop and to produce fruits below of 7° C. of temperature, the cold tolerance of 'Sahara' is Medium.

Drought tolerance: Applicant has not made any test about drought tolerance.

What is claimed is:

1. A new and distinct strawberry plant of the variety substantially as shown and described.

* * * * *

UNITED STATES PATENT AND TRADEMARK OFFICE

CERTIFICATE OF CORRECTION

PATENT NO. : PP26,289 P3
APPLICATION NO. : 13/987147
DATED : January 5, 2016
INVENTOR(S) : Alexandre Pierron-Darbonne It is certified that error appears in the above-identified patent and that said Letters Patent is hereby corrected as shown below:

On the title page of the Patent, below item (65) (line 26, approx.), please insert the following:

--(30) Foreign Application Priority Data

Jul. 5, 2012 (QZ)..... 2012/1505--

Signed and Sealed this
Fifteenth Day of March, 2016

Michelle K. Lee

Michelle K. Lee
*Director of the United States Patent and Trademark Office*